United States Patent [19]

Peterson

[11] 4,156,781

[45] May 29, 1979

[54] ω-ARYL-INTER-OXA-12,13(E)-DIDEHYDRO-13,14-DIHYDRO-PGD₁ COMPOUNDS

[75] Inventor: David C. Peterson, Portage, Mich.

[73] Assignee: The Upjohn Company, Kalamazoo, Mich.

[21] Appl. No.: 903,627

[22] Filed: May 8, 1978

Related U.S. Application Data

[62] Division of Ser. No. 809,249, Jun. 23, 1977, which is a division of Ser. No. 614,244, Sep. 17, 1975.

[51] Int. Cl.² .................................................. C07C 177/00
[52] U.S. Cl. ........................................ 560/53; 560/51; 562/463; 562/464
[58] Field of Search .................... 560/53, 51; 562/463, 562/464

*Primary Examiner*—Paul J. Killos
*Attorney, Agent, or Firm*—Robert A. Armitage

[57] ABSTRACT

Prostaglandin analogs with the following cyclopename ring structure:

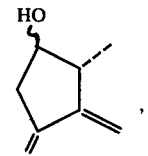

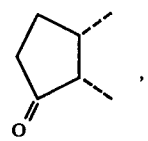

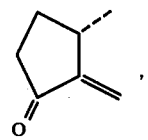

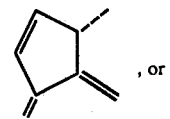

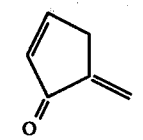

are disclosed along with intermediates useful in their preparation and processes for their preparation. These analogs are useful for some of the same pharmacological purposes as the prostaglandins, particularly and especially as blood platelet aggregation inhibitors.

55 Claims, No Drawings

ω-ARYL-INTER-OXA-12,13(E)-DIDEHYDRO-13,14-DIHYDRO-PGD₁ COMPOUNDS

The present application is a divisional application of Ser. No. 809,249, filed June 23, 1977; which is a divisional application of Ser. No. 614,244, filed Sept. 17, 1975, now pending. Likewise, U.S. Ser. No. 809,248, filed June 23, 1977 is a divisional application of Ser. No. 614,244.

The present invention relates to prostaglandin analogs for which the essential material constituting a disclosure therefor is incorporated by reference here from Ser. No. 809,248, now pending issuance as a United States patent.

I claim:

1. A prostaglandin analog of the formula

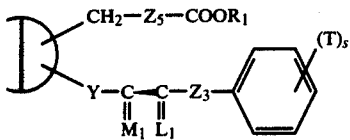

wherein D is

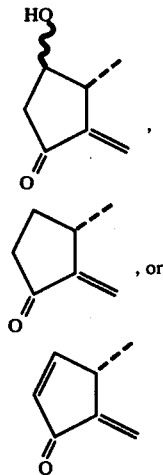

wherein Y is =CH—CH₂—;
wherein $Z_5$ is
(1) —CH₂—O—CH₂—(CH₂)$_g$—CH₂—,
(2) —(CH₂)₂—O—(CH₂)$_g$—CH₂—, or
(3) —(CH₂)₃—O—(CH₂)$_g$—,
wherein g is one, 2, or 3;
wherein $M_1$ is

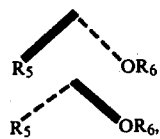

wherein $R_5$ and $R_6$ are hydrogen or methyl, with the proviso that one of $R_5$ and $R_6$ is methyl only when the other is hydrogen;
wherein $L_1$ is

or a mixture of

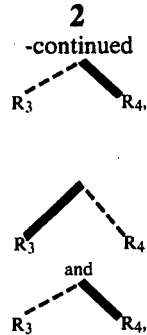

wherein $R_3$ and $R_4$ are hydrogen, methyl, or fluoro, being the same or different, with the proviso that one of $R_3$ and $R_4$ is hydrogen or fluoro only when the other is hydrogen or fluoro;
wherein $Z_3$ is oxa or methylene;
wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $Z_3$ is oxa only when $R_3$ and $R_4$ are hydrogen or methyl, being the same or different; and
$R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein $M_1$ is

3. A compound according to claim 1, wherein $M_1$ is

4. A compound according to claim 1, wherein D is

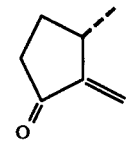

5. A compound according to claim 1, wherein $Z_3$ is methylene.

6. A compound according to claim 5, wherein s is zero or one and T is chloro, fluoro, or trifluoromethyl.

7. A compound according to claim 6, wherein g is one.

8. A compound according to claim 7, wherein $R_5$ and $R_6$ are both hydrogen.

9. A compound according to claim 8, wherein $R_3$ and $R_4$ are both hydrogen.

10. 5-Oxa-17-phenyl-18,19,20-trinor-13,14-dihydro-12,13(E)-didehydro-9-deoxy-PGD₁, a compound according to claim 9.

11. A compound according to claim 4, wherein $Z_3$ is oxa.

12. A compound according to claim 11, wherein s is zero or one and T is chloro, fluoro, or trifluoromethyl.

13. A compound according to claim 12, wherein g is one.

14. A compound according to claim 13, wherein R$_5$ and R$_6$ are both hydrogen.

15. A compound according to claim 14, wherein R$_3$ and R$_4$ are both hydrogen.

16. 5-Oxa-16-phenoxy-17,18,19,20-tetranor-13,14-dihydro12,13(E)-didehydro-9-deoxy-PGD$_1$, a compound according to claim 15.

17. A compound according to claim 4, wherein D is

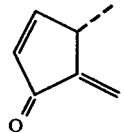

18. A compound according to claim 17, wherein Z$_3$ is methylene.

19. A compound according to claim 18, wherein s is zero or one and T is chloro, fluoro, or trifluoromethyl.

20. A compound according to claim 19, wherein g is one.

21. A compound according to claim 20, wherein R$_5$ and R$_6$ are both hydrogen.

22. A compound according to claim 21, wherein R$_3$ and R$_4$ are both hydrogen.

23. 5-Oxa-17-phenyl-18,19,20-trinor-12,13(E)-didehydro-13,14-dihydro-9,10-didehydro-9-deoxy-PGD$_1$, a compound according to claim 22.

24. A compound according to claim 17, wherein Z$_3$ is oxa.

25. A compound according to claim 24, wherein s is zero or one and T is chloro, fluoro, or trifluoromethyl.

26. A compound according to claim 25, wherein g is one.

27. A compound according to claim 26, wherein R$_5$ and R$_6$ are both hydrogen.

28. A compound according to claim 27, wherein R$_3$ and R$_4$ are both hydrogen.

29. 5-Oxa-16-phenoxy-17,18,19,20-tetranor-12,13(E)-didehydro-13,14-dihydro-9,10-didehydro-9-deoxy-PGD$_1$, a compound according to claim 28.

30. A compound according to claim 3, wherein D is

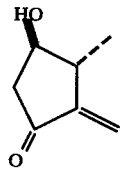

31. A compound according to claim 30, wherein Z$_3$ is methylene.

32. A compound according to claim 31, wherein s is zero or one and T is chloro, fluoro, or trifluoromethyl.

33. A compound according to claim 32, wherein g is one.

34. A compound according to claim 33, wherein R$_5$ and R$_6$ are both hydrogen.

35. A compound according to claim 34, wherein R$_3$ and R$_4$ are both hydrogen.

36. 5-Oxa-17-phenyl-18,19,20-trinor-12,13(E)-didehydro-13,14-dihydro-9β-PGD$_1$, a compound according to claim 35.

37. A compound according to claim 30, where Z$_3$ is oxa.

38. A compound according to claim 37, wherein s is zero or one and T is chloro, fluoro, or trifluoromethyl.

39. A compound according to claim 38, wherein g is one.

40. A compound according to claim 39, wherein R$_5$ and R$_6$ are both hydrogen.

41. A compound according to claim 40, wherein R$_3$ and R$_4$ are both hydrogen.

42. 5-Oxa-16-phenoxy-17,18,19,20-tetranor-12,13(E)-didehydro-13,14-dihydro-9β-PGD$_1$, a compound according to claim 41.

43. A compound according to claim 3, wherein D is

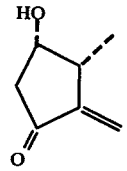

44. A compound according to claim 43, wherein Z$_3$ is methylene.

45. A compound according to claim 44, wherein s is zero or one and T is chloro, fluoro, or trifluoromethyl.

46. A compound according to claim 45, wherein g is one.

47. A compound according to claim 46, wherein R$_5$ and R$_6$ are both hydrogen.

48. A compound according to claim 47, wherein R$_3$ and R$_4$ are both hydrogen.

49. 5-Oxa-17-phenyl-18,19,20-trinor-12,13(E)-didehydro-13,14-dihydro-PGD$_1$, a compound according to claim 48.

50. A compound according to claim 43, wherein Z$_3$ is oxa.

51. A compound according to claim 50, wherein s is zero or one and T is chloro, fluoro, or trifluoromethyl.

52. A compound according to claim 51, wherein g is one.

53. A compound according to claim 52, wherein R$_5$ and R$_6$ are both hydrogen.

54. A compound according to claim 53, wherein R$_3$ and R$_4$ are both hydrogen.

55. 5-Oxa-16-phenoxy-17,18,19,20-tetranor-12,13(E)-didehydro-13,14-dihydro-PGD$_1$, a compound according to claim 54.

* * * * *

UNITED STATES PATENT OFFICE
CERTIFICATE OF CORRECTION

Patent No. 4,156,781     Dated    29 May 1979

Inventor(s)    David C. Peterson

It is certified that error appears in the above-identified patent and that said Letters Patent are hereby corrected as shown below:

Column 1, lines 5-10, should read as follows instead of as appears in the Letters Patent:
-- The present application is a divisional application of Serial No. 809,249, filed June 23, 1977, now U.S. Patent 4,142,052 issued Febraury 27, 1979; which is a divisional application of Serial No. 614,244, filed September 17, 1975, now pending. Likewise, United States Serial No. 809,248, filed June 23, 1977, now U.S. Patent 4,099,014 issued on July 4, 1978, is a divisional application of S.N. 614,244. --.
lines 14-16 should read -- United States Patent 4,099,014 --.

Column 2, line 44, should read -- according to claim 3, --;

Column 3, line 10, should read -- according to claim 3, --.

Signed and Sealed this

Twentieth Day of November 1979

[SEAL]

Attest:

RUTH C. MASON
Attesting Officer

LUTRELLE F. PARKER
Acting Commissioner of Patents and Trademarks